(12) United States Patent
Montpetit

(10) Patent No.: US 8,708,887 B2
(45) Date of Patent: Apr. 29, 2014

(54) MINIMALLY INVASIVE LEVATOR AVULSION REPAIR

(75) Inventor: Karen Pilney Montpetit, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 526 days.

(21) Appl. No.: 12/994,982

(22) PCT Filed: May 29, 2009

(86) PCT No.: PCT/US2009/003300
§ 371 (c)(1),
(2), (4) Date: Nov. 29, 2010

(87) PCT Pub. No.: WO2009/145911
PCT Pub. Date: Dec. 3, 2009

(65) Prior Publication Data
US 2011/0082331 A1    Apr. 7, 2011

Related U.S. Application Data

(60) Provisional application No. 61/057,027, filed on May 29, 2008.

(51) Int. Cl.
*A61F 2/00*  (2006.01)
(52) U.S. Cl.
USPC .......................................................... 600/37
(58) Field of Classification Search
USPC .................... 600/29–31, 37; 606/139–158; 623/23.64–23.71
See application file for complete search history.

(56) References Cited

U.S. PATENT DOCUMENTS

| | | | |
|---|---|---|---|
| 4,741,330 A | 5/1988 | Hayhurst | |
| 4,881,526 A * | 11/1989 | Johnson et al. | ............ 601/15 |
| 5,368,602 A | 11/1994 | De La Torre | |
| 5,647,836 A | 7/1997 | Blake, III et al. | |
| 6,354,991 B1 | 3/2002 | Gross et al. | |
| 6,382,214 B1 | 5/2002 | Raz et al. | |
| 6,612,977 B2 | 9/2003 | Staskin et al. | |
| 6,641,524 B2 | 11/2003 | Kovac | |
| 6,641,525 B2 | 11/2003 | Rocheleau et al. | |
| 6,652,449 B1 | 11/2003 | Gross et al. | |

(Continued)

FOREIGN PATENT DOCUMENTS

| | | |
|---|---|---|
| WO | WO 03/077772 | 9/2003 |
| WO | WO03077772 A1 | 9/2003 |

(Continued)

*Primary Examiner* — Charles A Marmor, II
*Assistant Examiner* — Catherine E Burk
(74) *Attorney, Agent, or Firm* — Kagan Binder, PLLC

(57) ABSTRACT

Described are pelvic implants and methods of surgically placing pelvic implants that provide treatment for pelvic floor disorders by support of the levator by creating an incision that allows access to a region of tissue of the pelvic floor and inserting a pelvic implant comprising a tissue support portion delivered by a delivery tool. A pelvic implant for supporting levator tissue comprising: a tissue support portion having a first end and a second; a tissue fastener disposed on the first end of the tissue support portion for fastening it to levator tissue; a guide extension portion disposed on the second end of the tissue support portion; and a support backer member attachable to the guide extension portion to adjust a tension of the tissue support portion and concomitantly the levator tissue.

7 Claims, 15 Drawing Sheets

(56) References Cited

U.S. PATENT DOCUMENTS

| | | | |
|---|---|---|---|
| 6,652,450 B2 | 11/2003 | Neisz et al. | |
| 6,669,735 B1 | 12/2003 | Pelissier | |
| 6,712,772 B2 | 3/2004 | Cohen et al. | |
| 6,802,807 B2 | 10/2004 | Anderson et al. | |
| 6,862,480 B2 | 3/2005 | Cohen et al. | |
| 6,896,651 B2 | 5/2005 | Gross et al. | |
| 6,911,003 B2 | 6/2005 | Anderson et al. | |
| 6,971,986 B2 | 12/2005 | Staskin et al. | |
| 7,048,682 B2 | 5/2006 | Neisz et al. | |
| 7,070,556 B2 | 7/2006 | Anderson et al. | |
| 2002/0161382 A1 | 10/2002 | Neisz et al. | |
| 2003/0212305 A1 | 11/2003 | Anderson et al. | |
| 2004/0039453 A1 | 2/2004 | Anderson et al. | |
| 2005/0143618 A1 | 6/2005 | Anderson et al. | |
| 2005/0245787 A1 | 11/2005 | Cox et al. | |
| 2005/0250977 A1 | 11/2005 | Montpetit et al. | |
| 2006/0195011 A1 | 8/2006 | Arnal et al. | |
| 2006/0224038 A1 | 10/2006 | Rao | |
| 2006/0229493 A1* | 10/2006 | Weiser et al. | 600/37 |
| 2006/0252980 A1* | 11/2006 | Arnal et al. | 600/29 |
| 2006/0287571 A1 | 12/2006 | Gozzi et al. | |
| 2007/0062541 A1 | 3/2007 | Zhou et al. | |
| 2008/0021265 A1 | 1/2008 | Garbin et al. | |
| 2008/0027271 A1 | 1/2008 | Maccarone | |
| 2008/0045782 A1 | 2/2008 | Jimenez | |
| 2009/0062600 A1 | 3/2009 | Hallum | |
| 2009/0221868 A1* | 9/2009 | Evans | 600/37 |
| 2010/0105979 A1 | 4/2010 | Hamel et al. | |
| 2010/0261952 A1 | 10/2010 | Monetpetit et al. | |
| 2010/0261955 A1* | 10/2010 | O'Hern et al. | 600/37 |
| 2010/0305695 A1* | 12/2010 | Devonec | 623/7 |

FOREIGN PATENT DOCUMENTS

| | | |
|---|---|---|
| WO | WO03096929 A1 | 11/2003 |
| WO | WO2004045457 A1 | 6/2004 |
| WO | WO2005110274 A1 | 11/2005 |
| WO | WO2006069078 A2 | 6/2006 |
| WO | WO 2007/016083 | 2/2007 |
| WO | WO2007059368 A1 | 5/2007 |
| WO | WO2007081955 A1 | 7/2007 |
| WO | WO 2007/097994 | 8/2007 |
| WO | WO 2007/149348 | 12/2007 |
| WO | WO2007146784 A2 | 12/2007 |
| WO | WO2007149348 A2 | 12/2007 |
| WO | WO2008013867 A1 | 1/2008 |
| WO | WO2008015722 A1 | 2/2008 |
| WO | WO2008042438 A2 | 4/2008 |
| WO | WO2008057269 A1 | 5/2008 |
| WO | WO2008083394 A2 | 7/2008 |
| WO | WO2008124056 A1 | 10/2008 |
| WO | WO2009005714 A2 | 1/2009 |
| WO | WO2009011852 A1 | 1/2009 |
| WO | WO2009038781 A1 | 3/2009 |
| WO | WO2009075800 A1 | 6/2009 |
| WO | WO2009145911 A1 | 12/2009 |
| WO | WO2010129331 A2 | 11/2010 |

* cited by examiner

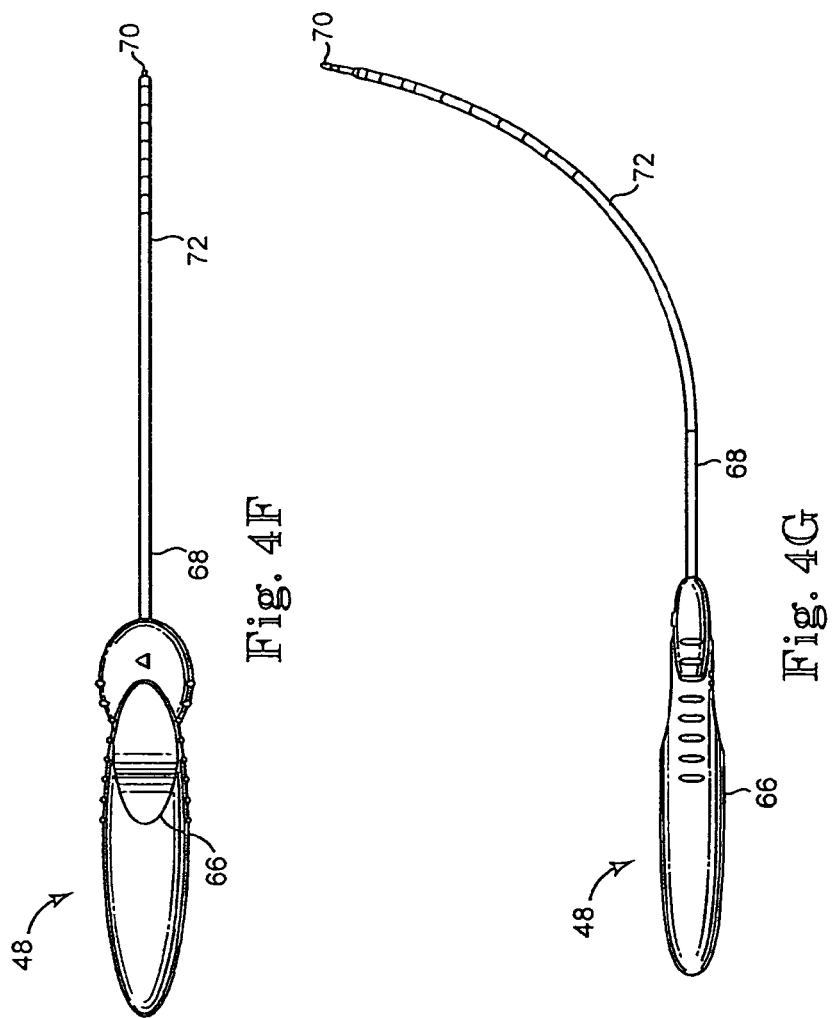

MINIMALLY INVASIVE LEVATOR AVULSION REPAIR

PRIORITY CLAIM

This application claims benefit from International Application No. PCT/US2009/003300, which was filed on May 29, 2009, which in turn claims priority to of U.S. Provisional Application Ser. No. 61/057,027, filed May 29, 2008, which applications are is incorporated herein by reference in their entireties.

FIELD OF THE INVENTION

The invention relates to apparatus and methods for treating pelvic conditions by use of a pelvic implant to support pelvic tissue. The pelvic conditions include conditions of the female or male anatomy, and specifically include treatments that involve supporting pelvic muscles and organs, such as to levator defects, female or male urinary and fecal incontinence, among other conditions.

BACKGROUND OF THE INVENTION

Pelvic health for men and women is a medical area of increasing importance, at least in part due to an aging population. Examples of common pelvic ailments include incontinence (fecal and urinary) and pelvic tissue prolapse (e.g., female levator bulging and vaginal prolapses). Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems, including the levator muscles.

Pelvic implants, sometimes referred to as slings, hammocks, have been introduced for implantation in the body to treat pelvic conditions such as prolapse and incontinence conditions. See, for example, commonly assigned U.S. Pat. Nos. 6,382,214, 6,641,524, 6,652,450, and 6,911,003, and publications and patents cited therein, each of which are incorporated herein in their entirety by reference. The implantation of these implants involves the use of implantation tools that create transvaginal, transobturator, supra-pubic, or retro-pubic exposures or pathways. A delivery system for coupling the sling ends to ends of elongate insertion tools, to draw sling extension portions through tissue pathways, is also included.

One specific area of pelvic health is trauma of the pelvic floor, e.g., of the levator ("levator ani") or coccygeus muscle (collectively the pelvic floor). The pelvic floor is made up of the levator and coccygeus muscles, and the levator is made up of components that include the puborectalis muscle, the pubococcygeus muscle, and the iliococcygeous muscle. For various reasons, the levator may suffer weakness or injury that can result in various symptoms such as prolapse, incontinence, and other conditions of the pelvis.

SUMMARY OF THE INVENTION

The invention relates to methods of treating pelvic conditions, especially by supporting levator tissue. Levator defects (weakness or injury) can affect any portion of the levator, and can be especially common in the pubic portion of the levator ani, including the pubococcygeus and puborectalis muscles. Such defects are relatively common, for instance, in women with vaginal prolapse. Defects can also be present at the iliococcygeus muscle. Still other defects are in the form of a paravaginal defect, such as avulsion of the inferiomedial aspects of the levator ani from the pelvic sidewall; avulsion can refer to tissue being detached from the pubic bone, and may precede prolapse conditions. Another levator defect is levator ballooning, which refers to distension of levator muscles.

A different levator defect is a defect of the levator hiatus, which can reduce the stability of the pelvic floor and may result in sexual dysfunction, defecatory dysfunction, rectal prolapse, and fecal incontinence and possibly urinary incontinence. Levator hiatus is also believed to play a significant role in the progression of prolapse. Embodiments of methods of the invention can address any of the conditions, as well as related conditions and symptoms.

The present patent application describes pelvic implants and methods for treating pelvic conditions by treating defects of the pelvic floor (coccygeus or levator), such as weakness or injury, or by otherwise supporting levator muscle. Useful methods can involve methods and implants that can restore natural pelvic floor anatomy using an implant (e.g., graft) in the form of a hammock, sling, and the like, to augment injured, weakened, or attenuated levator musculature. The levator musculature or "levator ani" can include the puborectalis, pubococcygeus, iliococcygeus, among others.

Embodiments of implants useful according to the invention can be of a size and shape to address a desired pelvic floor condition, generally of a size and shape to conform to levator tissue, optionally to additionally contact or support other tissue of the pelvic region such as the anal sphincter, rectum, perineal body, etc. The implant can be of a single or multiple pieces that is or are shaped overall to match a portion of the levator, e.g., that is circular, oblong trapezoidal, rectangular, that contains a combination of straight, angled, and arcuate edges, etc. The implant may include attached or separate segments that fit together to extend beside or around pelvic features such as the rectum, anus, vagina, and the like, optionally to attach to the feature.

In one embodiment, the implant can include a tissue support portion, which may contact levator tissue upon implantation. The implant can additionally include one or more guide extension portions that extends beyond the tissue support portion and extend out of an incision to guide a support backer member that may be used to tension the tissue support portion of the implant.

Optionally, the tissue support portion can include one or more tissue fasteners (e.g., self-fixating tip, soft tissue anchor, etc.), connected to a portion of the tissue support portion in order to fix the tissue support portion to tissue. A sheath may also be provided that extends over at least a portion of the tissue support portion to aid in easing implantation.

In an example embodiment, the tissue support portion and optionally the guide extension portion, tissue fastener, etc., may optionally be coated with antimicrobial coatings to prevent infection or coatings to encourage ingrowth or inhibit rejection. For tissue support portions and extension portions, biocompatible materials are contemplated such as porcine dermis or meshes with growth factors.

A method as described herein may improve or treat a condition of the pelvic region, such as any of the pelvic conditions described. The method may support levator tissue, for treatment of prolapse; fecal incontinence; a torn, weakened, or damaged levator muscle (meaning any portion of the levator muscle); levator avulsion, levator ballooning, treatment to support a perineal body; a method of perineal body repair; a method of treating the levator hiatus by tightening or reducing the size of the levator hiatus; and combinations of one or more of these. The method may also be more general, as a treatment of more general conditions such as urinary continence that is believed to be caused by or contributed to by a weakened levator.

The method may be prophylactic or medically necessary. A prophylactic treatment may be a preventative treatment for potential disease or condition that does not yet exist but that may be likely to exist. For example preventative treatment may be useful upon a grade one or two prolapse, for reinforcement of current prolapse repair, or post-partum. A medically necessary procedure may take place when a disease is present and in need of immediate treatment, such as in the case of perineal descent, fecal incontinence, urinary incontinence, reinforcement of current prolapse repair, and rectal prolapse.

An implant can be placed to contact pelvic tissue as desired, to support the tissue, such as levator tissue, and can optionally be secured to the tissue to be supported, e.g., by suturing or anchoring. The implant can additionally be secured to tissue of the pelvic region for additional support, such as to tissue such as: sacrotuberous ligament; sacrospinous ligament; anococcygeal ligament ("anococcygeal body ligament"); periostium of the pubic bone (e.g., in a region of the ischial tuberosity); pubourethral ligament; ischial spine (e.g., at a region of the ischial spine); ischial tuberosity; arcus tendineus (used synonymously herein with the term "white line"), e.g., through a tissue path between levator ani muscle and obturator internus muscle and attached at the arcus tendineus; obturator internus muscle. Alternately, an extension guide portion of an implant can be extended through a tissue path that leads to an external incision such as: by passing through tissue of the obturator foramen.

According to exemplary methods, an implant can be introduced through an incision that allows access to levator tissue, optionally with or without some amount of dissection. The incision can be any of a variety of incisions that provide such access, such as a small external perirectal incision that can allow a tissue path to extend from the external perirectal incision to levator tissue; an external suprapubic incision; an external incision that can be used to pass a portion of an implant through an obturator foramen, a Kraske incision under the rectum; an incision at the perineum; and a vaginal incision. An implant or a portion of the implant can be accessed or placed into position using the incision, to support tissue of the levator. Preferably the implant can be placed by dissecting a plane or region of dissection that includes the ischorectal fossa. Anatomical landmarks included with this region of dissection can include the ischial spine, the obturator internus, the arcus tendineus.

One embodiment of implant can be a synthetic or biologic implant having a tissue support portion. The tissue support portion can be sized and shaped to support levator tissue. The precise form can depend on the type of condition being treated. Certain embodiments of a tissue support portion may optionally include a segment or support for addressing levator hiatus opening, perineal descent, rectal prolapse, fecal incontinence, etc.

The invention contemplates various methods of supporting levator tissue. Exemplary methods include steps that involve creating a single medial incision (a transvaginal incision or a perineal incision) or an incision near the rectum, anus, or perineum; and dissecting within a plane or region of dissection including the ischorectal fossa. An implant can be inserted to contact tissue of the levator, over a desired area.

Optionally, the implant can be a single piece or multiple pieces or portions, and may include one or more tissue fasteners that can be secured to tissue in the pelvic region. An implant may include materials or components such as those used in the Elevate, MiniArc, SPARC and Monarc systems (from American Medical Systems), include connectors for engagement between a needle of an insertion tool and an distal end of an extension portion, as well as helical, straight, and curved needles.

In one aspect, the invention relates to pelvic implant for supporting tissue of the pelvic floor (e.g., levator tissue, coccygeus tissue, or combinations of these), and related surgical systems and kits. In another aspect, the invention provides a system and method of repairing levator avulsion. Namely, a small incision can be made to deploy a relatively small implant, with anchoring device, unilaterally or bilaterally. The implant is delivered and deployed via a needle or introducer device that can be anatomically (curved, helical, etc.) shaped and configured for traversal along the vaginal sidewall to advance through the obturator membrane such that a first anchor of the implant is securable to or proximate the tissue defect or avulsion. The needle and implant are then retrieved or withdrawn, with the anchored tissue being pulled back to or proximate the tissue tear site or damaged area. At this point, adjustment can be made to the anchor devices, implant length, or by employing other known adjustment systems or methods to remove slack in the implant or facilitate tautness in the repaired tissue.

Various implant and anchoring devices can be implemented for the present invention. For instance, various mesh supports and fixating anchoring end portions can be employed.

BRIEF DESCRIPTION OF DRAWINGS

Other features and advantages of the present invention will be seen as the following description of particular embodiments progresses in conjunction with the drawings. Drawings are schematic and not to scale.

FIGS. 4B-4G illustrates example embodiments of delivery tools.

Figure 1A:
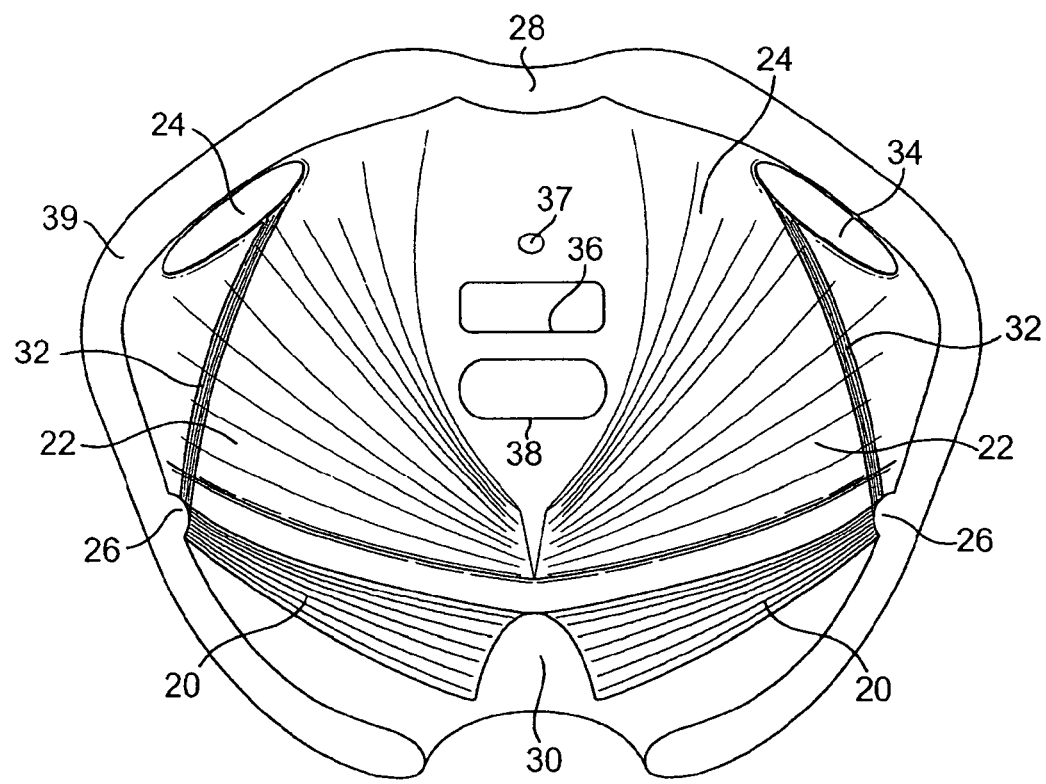
FIG. 1A illustrates example of health anatomy of a pelvic region.

The preceding description of the drawings is provided for example purposes only and should not be considered limiting. The following detailed description is provided for more detailed examples of the invention. Other embodiments not disclosed or directly discussed are also considered to be within the scope and spirit of the invention. It is not the intention of the inventor to limit the scope of the invention by describing one or more example embodiments.

DETAILED DESCRIPTION

The following description is meant to be illustrative only and not limiting. Other embodiments of this invention will be apparent to those of ordinary skill in the art in view of this description.

The invention relates to surgical implants, insertion tools, kits, and assemblies, and related methods for treating pelvic defect and disorders related to levator avulsion, ballooning, etc. As a secondary effect the methods of treating levator avulsion or ballooning may treat, improve, or prevent a condition such as prolapse, incontinence (urinary or fecal incontinence), conditions of the perineal body, conditions of the levator hiatus, levator ballooning, and combinations of two or more of these.

According to various embodiments, a surgical implant can be used to support levator tissue in a region of a levator avulsion. The implant may be placed to contact or support levator tissue at a location in a region of a levator avulsion. A "region of a levator avulsion" refers to a location of levator tissue that can be contacted by a support portion of an implant to allow the implant to be manipulated or tensioned in a manner that will cause approximation of tissue of the levator muscle, to at least in part remedy the avulsion; the region may be at a surface of the levator tissue or at a location at an interior of the tissue, and may be at a location that is considered to be either "inferior" to ("caudal" to) the avulsed tissue or "superior" to the avulsed tissue; optionally the region can be proximal to the avulsion, such as within 3 centimeters, within 2 centimeters, or within 1 centimeter from tissue of an avulsion.

As an example, a portion of implant (e.g., a portion of support portion, such as a short length of the support portion) can be placed within the tissue of the levator muscle ("embedded" in the muscle or "tunneled" through a length of the muscle). According to such an example, a portion of implant may enter (or exit) levator tissue inferior to the avulsed tissue, be embedded in the belly of the levator muscle and extend through an obturator foramen. Alternately, the implant may extend through the levator muscle tissue inferior to the avulsed tissue, traverse the avulsion, and continue on a superior side of the avulsion, then exit at a location superior to the avulsed tissue, such as at a location near the obturator internus muscle. Generally, the implant can exit the levator muscle tissue on the obturator internus side of the levator muscle, extend through tissue of the obturator internus muscle, through the obturator foramen, toward the anterior external incision, and exit the patient at the anterior incision.

The implant can be used to support the levator tissue to remedy a levator avulsion such as by approximating levator tissue, supporting levator tissue, or both, to cause levator tissue to move to close the avulsion. In the event that an avulsion involves a detachment of levator tissue from tissue or bone at a superior region of levator tissue—e.g., a detachment at or near tissue of an arcus tendineus, tissue of an obturator internus muscle, a pubic bone, an ischial spine, or any combination of these–the levator tissue can be approximated in a direction to allow the detached tissue to be moved closer to the location of the detachment. After this tissue approximation, the implant can be maintained in the implanted position to continue to support the levator tissue to prevent subsequent return of the levator muscle to the avulsed condition, and to potentially prevent future conditions of avulsion or related prolapse, incontinence, levator ballooning, or other pelvic condition.

Turning now to the figures, FIG. 1 shows anatomy relevant to methods and devices of embodiments of the invention. In particular, FIG. 1, illustrates a superior view of tissue at different levels of the pelvic region, including ischiococcygeous muscle 20, iliococcygeus muscle 22, puborectalis and pubococcygeous muscles 24, ischial spine 26, pubic symphasis 228, coccyx 30, arcus tendineus 32, and obturator foramen 34. Vagina 36, urethra 37, rectum 38, and pelvic bone 39 are also shown. Continuing with FIG. 1, a levator avulsion (not illustrated) may typically be located along the superior portion of the levator muscle extending between the ischial spine, along the arcus tendineus, and to the obturator internus muscle, for example at a superior portion of any one or more of the puborectalis muscle, pubococcygeus muscle, or iliococcygeous muscle. According to embodiments of the invention, an implant can be placed to approximate, support, or approximate and support, one or more of these muscles to treat the avulsion.

Figure 1B:
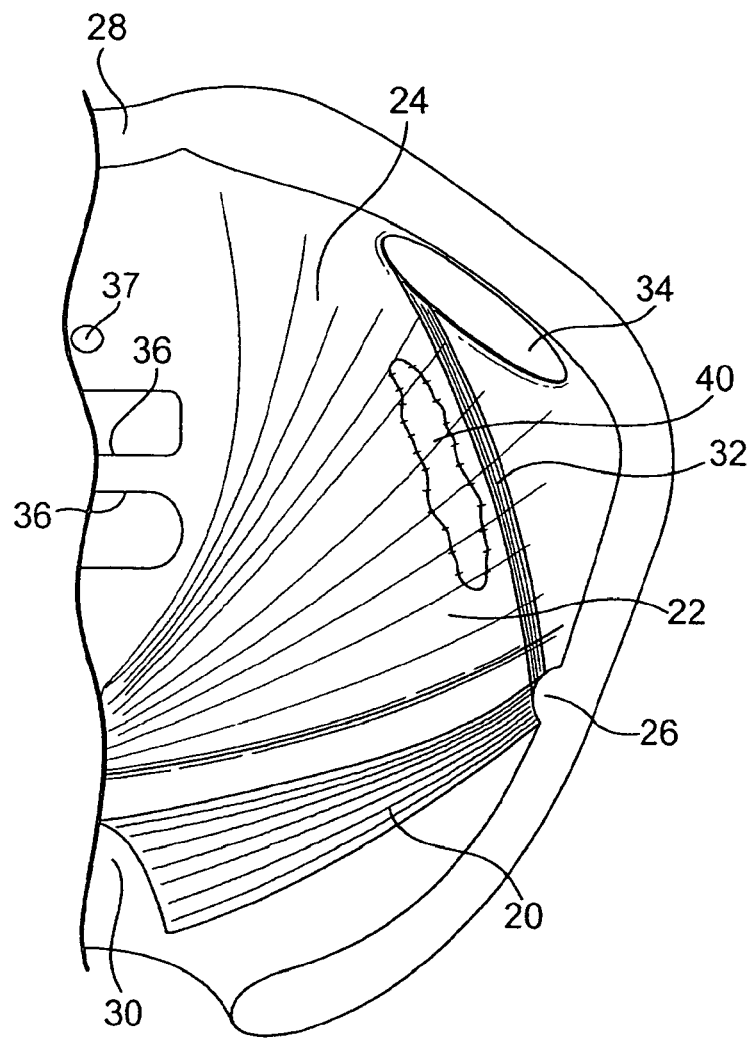
FIG. 1B illustrates example of a pelvic region having a defect.

FIG. 1B illustrates relevant anatomy (on a patient's right side), as described, and includes an exemplary depiction of avulsion 40. Although the avulsion is demonstrated as being located in the iliococcygeus muscle it should be understood that the avulsion could be located in any of the pelvic muscles and the implant of the present invention may be used to repair such defect.

Figure 2:
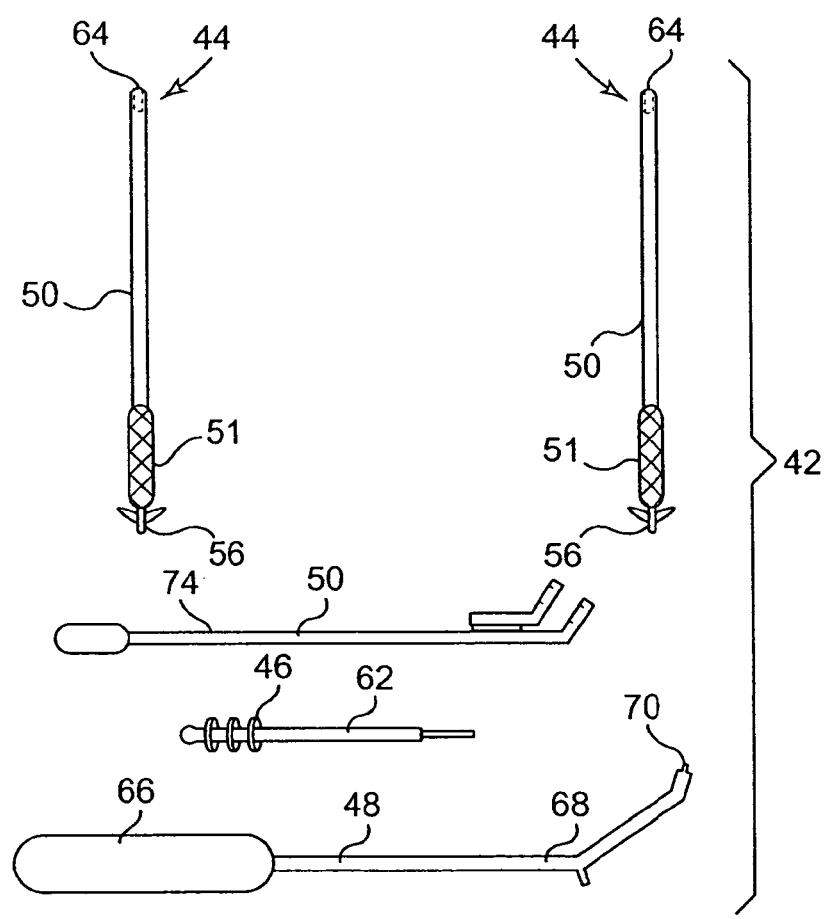
FIG. 2 illustrates exemplary features or components of the invention for repairing defects in pelvic anatomy.

Generally, FIG. 2 illustrates various parts or components of the pelvic defect repair system 42. FIG. 2 shows an implant 44 with one-way frictional adjusting engagement members or support backer members 46. The system 42 may also include an implant delivery device 48 to deliver the implant 44 to a tissue approximate a defect and a backer delivery device 50 to deliver one or more support backer members 46 to a tissue used to support the tissue via the implant 44.

Figure 3A:
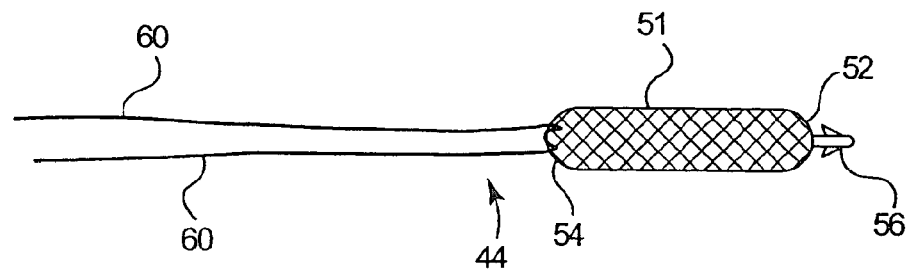
FIG. 3A illustrates an exemplary implant of the invention.
Figure 3B:
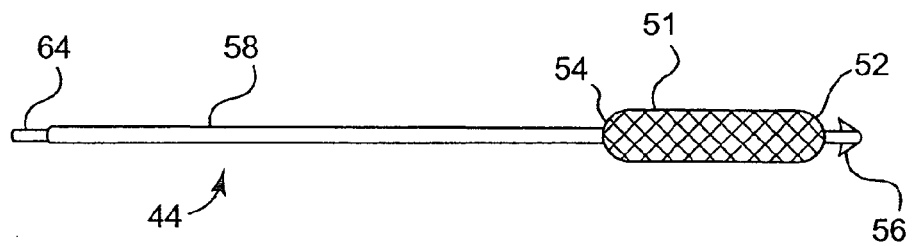
FIG. 3B illustrates an exemplary implant of the invention.

As particularly illustrated in FIGS. 3A and 3B, the implant 44 may include a tissue support portion 51 made from any material capable of permitting tissue ingrowth such as synthetic or biological mesh materials. The tissue support portion 51 may have first 52 and second 54 opposed ends. Attached or connected to the first end 52 of the tissue support portion 51 may be a tissue anchor or self fixating tip 56 that is designed to engage tissue proximate a defect such that the tissue support portion 51 may support and/or contact the tissue proximate the defect. By contacting or connecting with the tissue proximate the defect the tissue support portion 51 may permit tissue ingrowth, thereby providing additional support to the musculature.

As particularly illustrated in FIG. 3B, the implant 44 may also have an extension guide portion 58 disposed on or connected to the second end 54 of the tissue support portion 51 to guide the support backer member(s) 46 toward a portion of the tissue support portion 51. In one embodiment, the extension guide 58 may comprise a generally rigid, generally flexible or bendable rod or shaft. In other embodiments, as illustrated in FIG. 3A the extension guide 58 may comprise one or more sutures 60 that are connected or sewn to a portion of the tissue support portion 51. In yet other embodiments, the extension guide 58 may comprise mesh, wire or any other material or structure capable of guiding the support backer member(s) 46 toward the tissue support portion 51.

Figure 3C:
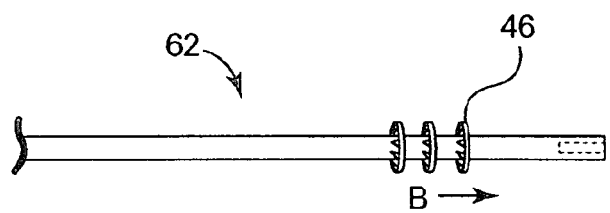
FIG. 3C illustrates a carrier for carrying support backer members of the invention.
Figure 3D:
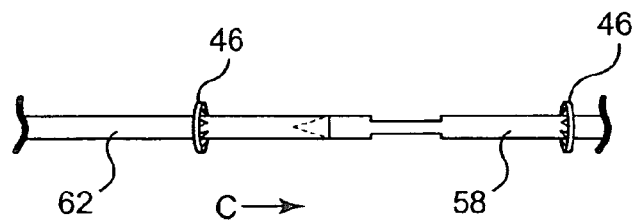
FIG. 3D illustrates a carrier for carrying support backer members of the invention coupled to a portion of the implant.

As illustrated in FIGS. 3C and 3D, the system 42 may also include a carrier 62 to carry and transfer one or more of the support backer members 46 to the extension guide portion 58. In one embodiment, the carrier 62 may comprise a rod or shaft having a mating feature such as a shaft having a reduced outer diameter or axially extending bore that can fit into or onto a free end 64 of the extension guide portion 58. The carrier 62 ensures that the support backer members 46 are properly transferred to the extension guide portion 58 of the implant 44.

Figure 4A:
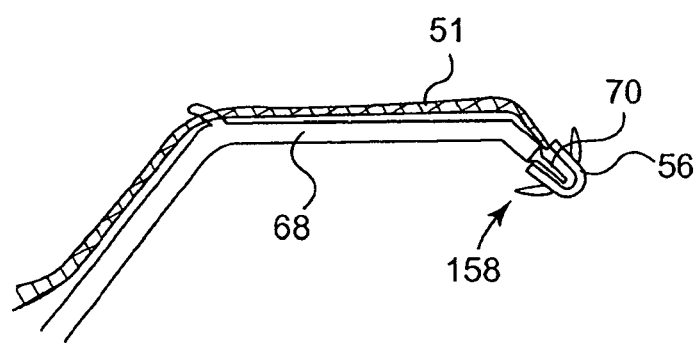
FIG. 4A illustrates an implant disposed upon a delivery tool.
Figure 4B:
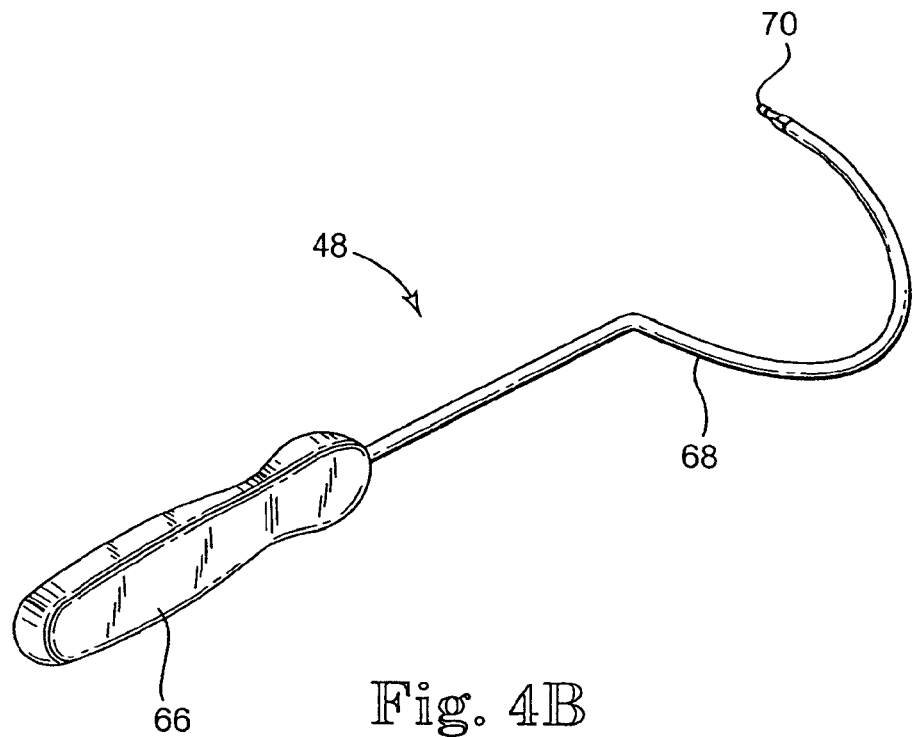
Figure 4C:
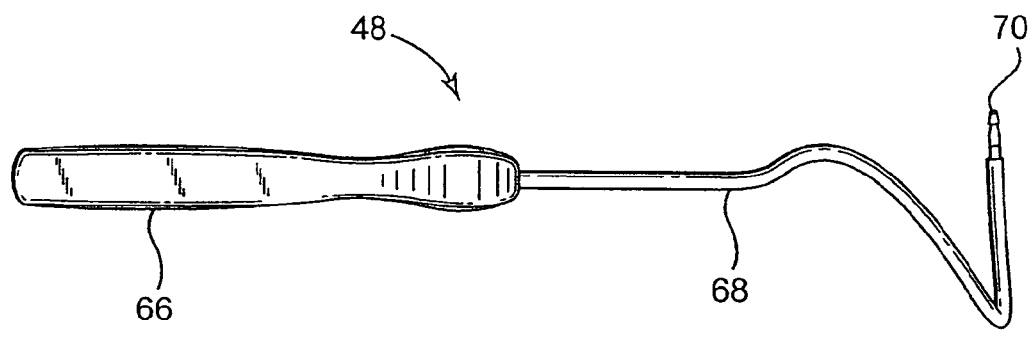
Figure 4D:
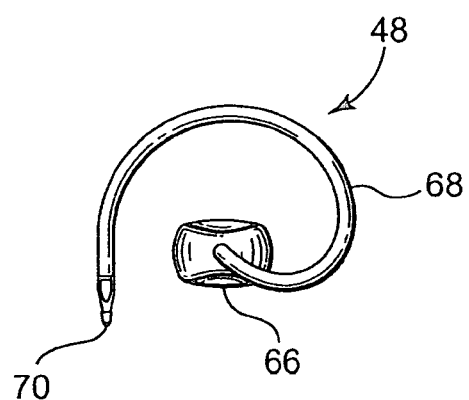
Figure 4E:
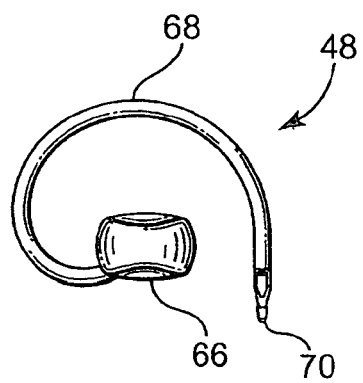

Turning to FIG. 4A, the implant delivery device 48 of the system 42 may include a handle 66 having a needle 68 extending away from a portion of the handle 66. As particularly illustrated in FIG. 4A, the self fixating tip 56 is designed to engaged, connect or couple to a tip or free end 70 of the needle 68. In one embodiment, the self fixating tip 56 may have a channel or bore that may be keyed to ensure proper connection between it and the free end 70 of the needle 68. The self fixating tip 56 may also be connected to the free end 70 of the needle 60 by a mechanism that permits controlled release into a tissue mass such as a levator muscle.

Referring to FIGS. 4B-4G, the needle 68 may have any of a variety of shapes to facilitate placement of the implant 44 in a therapeutic location designed to repair pelvic defects. As particularly illustrated in FIGS. 4B-4E, the needle 68 may have a portion between the handle 66 and its free end 70 that is generally helical. The system 42 may include multiple delivery tools 48 designed for insertion of the implant 44 in different anatomical locations such as the left and right obturator foramen. As particularly illustrated in FIGS. 4D and 4E, the needle 68 may be bent or have a slight bend located between the handle 66 and the free end 70 of the needle 68. The delivery tools 48 may be sterilized or disposable. The needle 68 may also have a number of notches or measurements 72 disposed along its length to permit a physician to determine a length of the needle 68 disposed in a patient.

Figure 5A:
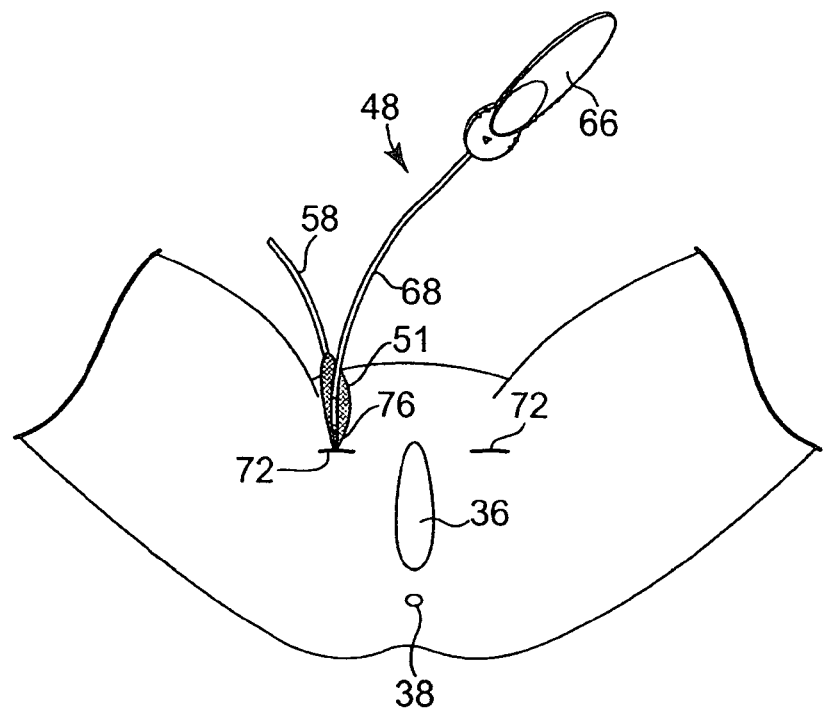
FIG. 5A illustrates an example of process for repairing a pelvic defect.
Figure 5B:
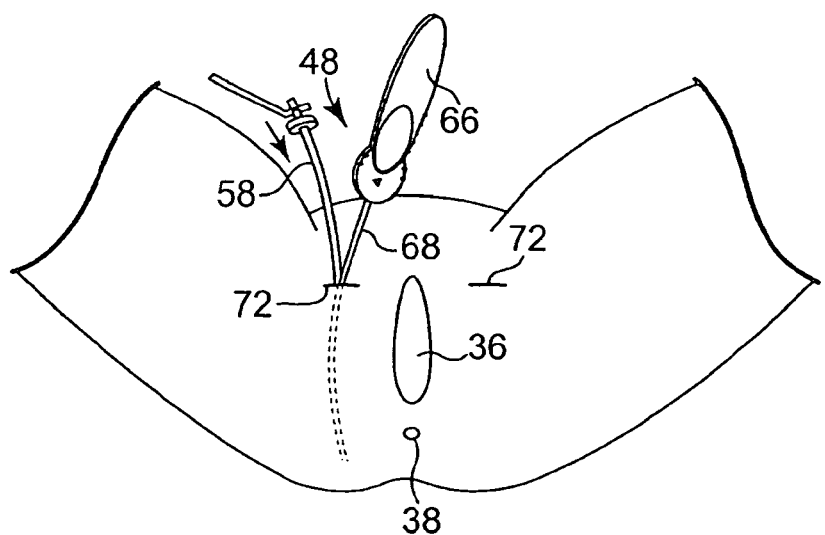
FIG. 5B illustrates another step in a process for repairing a pelvic defect.
Figure 5C:
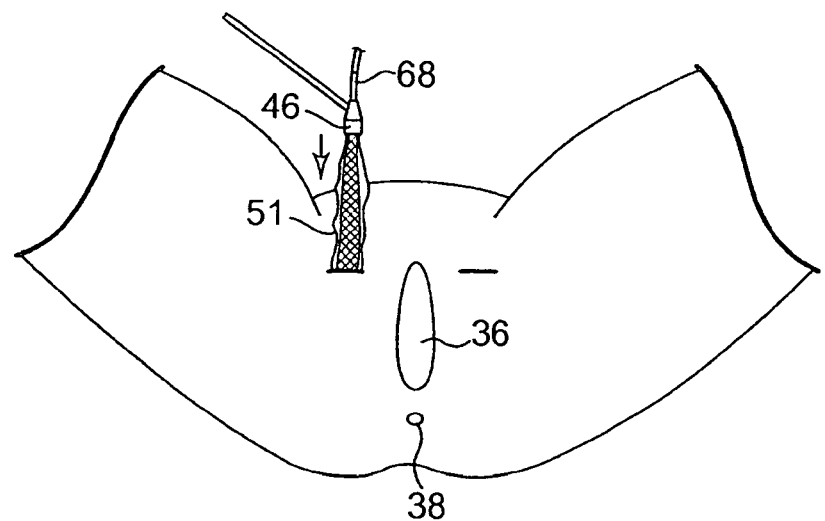
FIG. 5C illustrates another step in a process for repairing a pelvic defect.
Figure 5D:
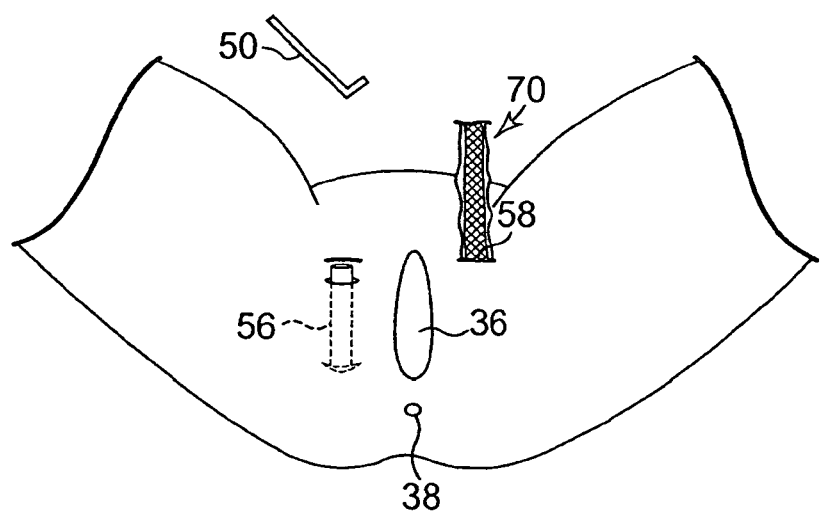
FIG. 5D illustrates another step in a process for repairing a pelvic defect.
Figure 10A:
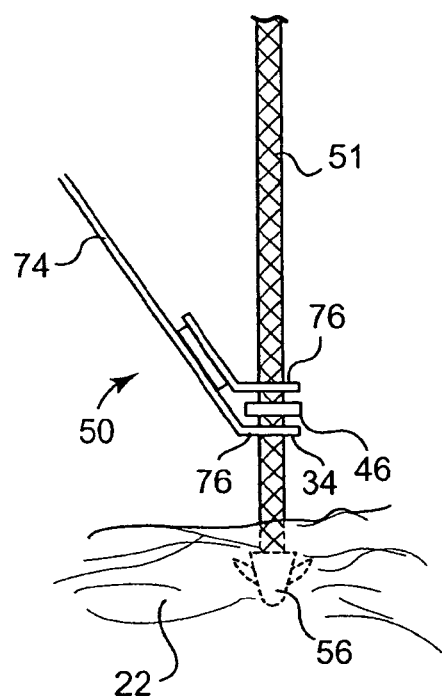
FIG. 10A illustrates an example of delivering the support backer member.
Figure 11A:
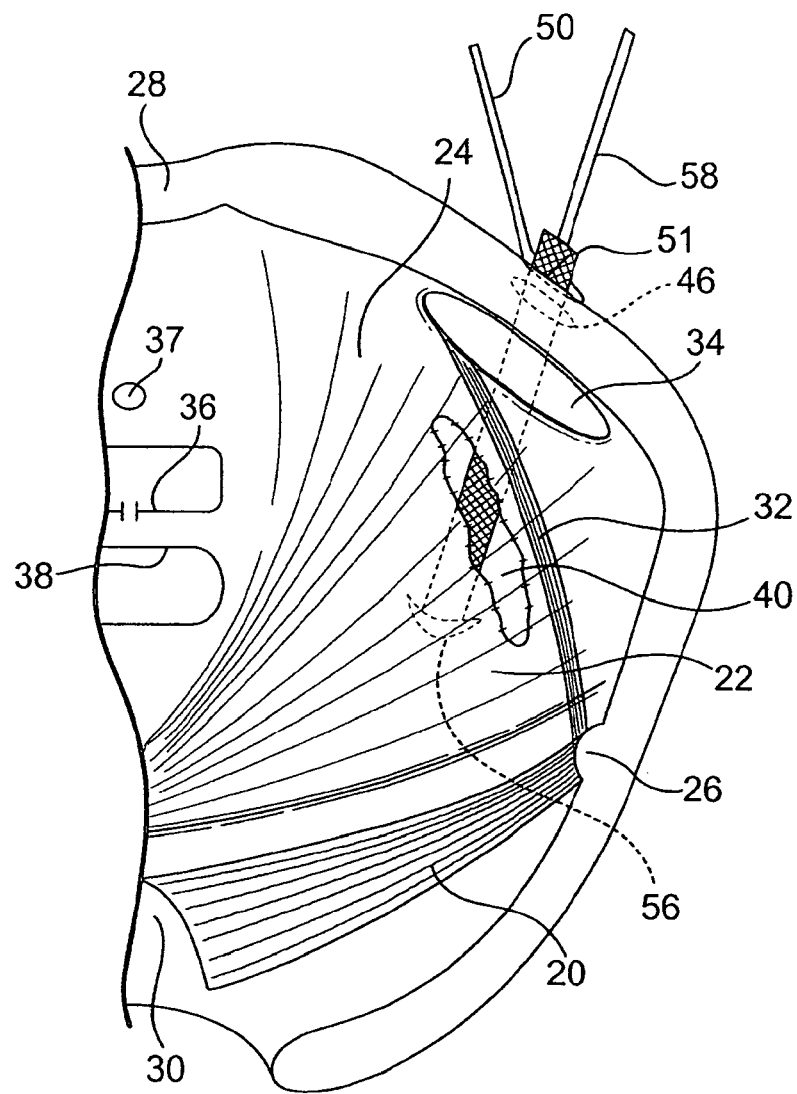
FIG. 11A illustrates an example of the implant prior to adjusting to repair a defect.
Figure 11B:
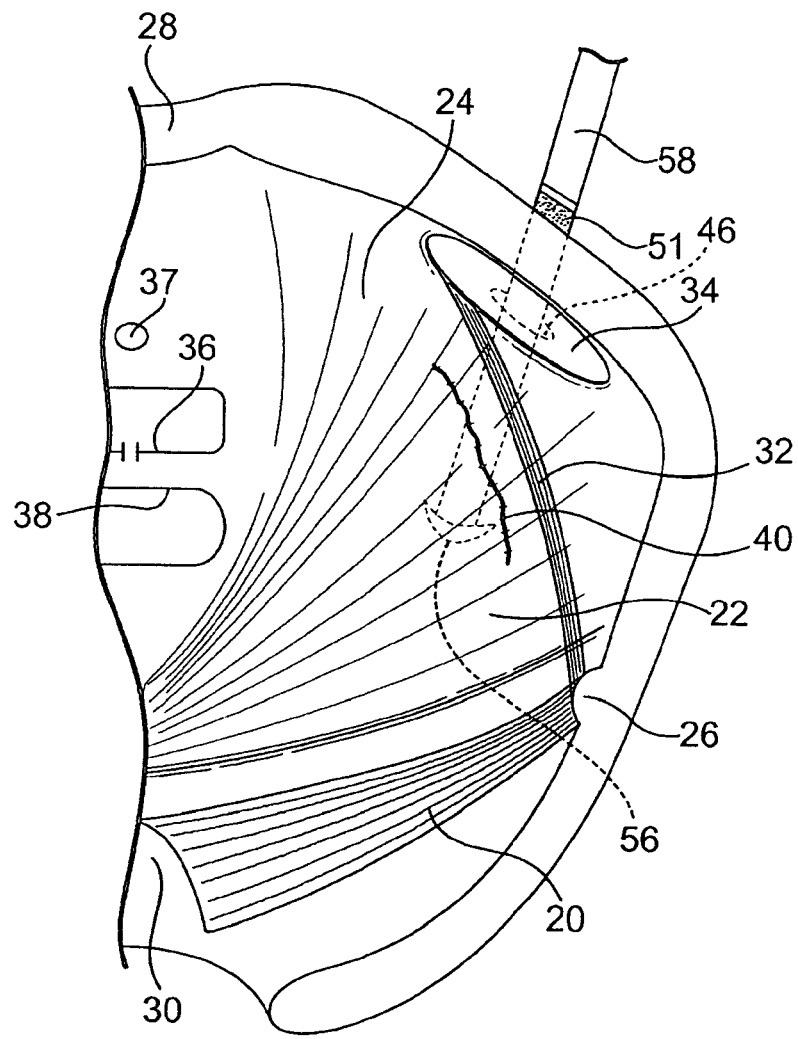
FIG. 11B illustrates an example of the implant after adjustment with a defect repaired.

As illustrated in FIG. 5A, an incision 72 can be made in a patient's dermis proximate their obturator foramen. A physician can attach the self fixating tip 56 to the free end 70 of the needle 68. The free end 70 of the needle 68 and the self fixating tip 56 can then be inserted into the incision 72. As illustrated in FIG. 5B, the needle 68 and self fixating tip 56 may be passed through the obturator foramen 34 (not shown) and into the levator tissue as shown in FIG. 10A. As particularly illustrated in FIG. 11A, the self fixating tip 56 may be inserted into levator muscle inferior the defect or any other tissue such as tissue surrounding the urethra or rectum.

As illustrated in FIG. 5B, the extension guide portion 58 of the implant 44 may extend out of the incision 72. At this particular point a physician may remove the delivery tool 48 or maintain it in contact with the implant 44. The carrier 62 can be coupled to the extension guide 58 and one or more support backer members 46 moved down onto the extension guide portion 58. The backer delivery device 50, which may comprise a shaft 74 having an engagement end 76 and an engagement configuration attached to or formed on the shaft 74 for engaging a support backer member 46, may be moved along the extension guide 58 to engage the support backer member 46 and move it through the incision 72.

Figure 6:
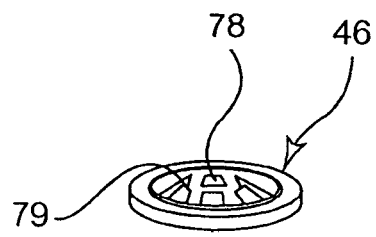
FIG. 6 illustrates an example of a support backer member.
Figure 7:
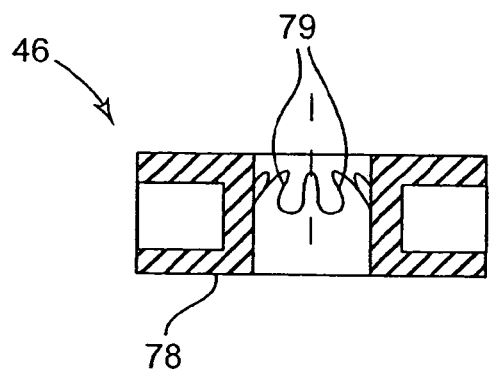
FIG. 7 illustrates a cross section of FIG. 6 above.
Figure 8A:
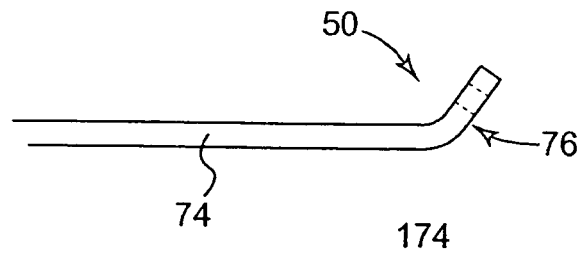
FIGS. 8A-9B illustrates example embodiments of delivery tools used to deliver the support backer member.
Figure 8B:
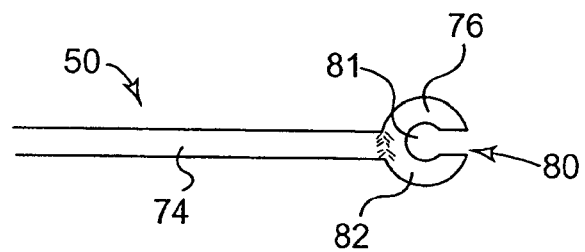

As the support backer member 46 is moved toward the obturator foramen by the backer delivery device 50 it engages the tissue support portion 51 of the implant 44. The support backer member 46, which may comprise a ring 78 having an aperture and a plurality of inwardly radiating engagement portions or flanges, flaps or teeth 79 (as illustrated in FIGS. 6 and 7) extending into the aperture engage the tissue support portion 51 of the implant 44. The support backer member 46 may be designed to permit movement along the extension guide portion 58 and onto the tissue support portion 51 but resist movement in a reverse direction. As the support backer member 46 is disposed proximate the obturator foramen the physician may pull on the extension guide portion 58 to place the tissue support portion 51 in tension. In another embodiment, the physician may permit a predetermined amount of slack in the tissue support portion 51 between the obturator foramen and the self fixating tip 56 in the tissue to create a backstop for organs and/or tissue.

Figure 9A:
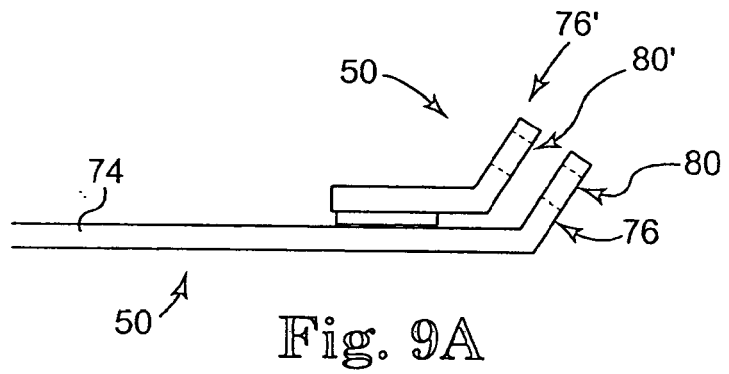
Figure 9B:
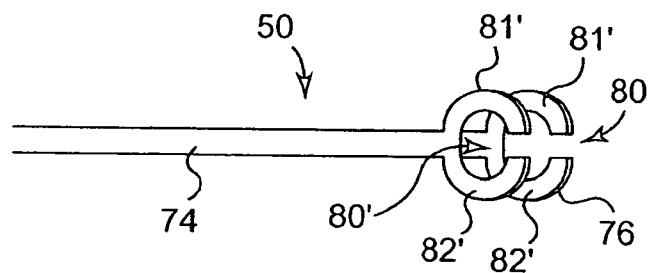

In one embodiment, the engagement end 76 of the backer member delivery device 50 may include one or more solid rings and aperture 80 or arms 81 and 82 defining an opening for receiving the extension guide portion 58. In one embodiment of the invention, as illustrated in FIGS. 9A and 9B, the engagement end 76 may include multiple apertures 80, 80' and/or arms 81, 81' and 82, 82'. In this particular embodiment, a backer member 46 can be disposed between the pairs of arms 81, 81' and 82, 82'. The aperture 80 or apertures 80 and 80' may have a central axis that is generally parallel to or generally angled to a longitudinal axis of the shaft 74 of the backer member delivery tool 50. The shaft 74 of the backer delivery tool 50 may have spaced apart notches, markings and the like to permit a physician to determine a length or depth of the backer member delivery tool 50 disposed in a patient.

The following patent documents are incorporated herein by reference to permit one skilled in the art to better understand the invention and its various embodiments: US Patent Publication No. US 2004/0039453 A1; US Patent Publication No. US 2005/0250977 A1; US Patent Publication No. US 2005/0245787 A1; U.S. Pat. No. 6,652,450; U.S. Pat. No. 6,612,977; U.S. Pat. No. 6,802,807; U.S. Pat. No. 7,048,682; U.S. Pat. No. 6,641,525; U.S. Pat. No. 6,911,003; U.S. Pat. No. 7,070,556; U.S. Pat. No. 6,354,991; U.S. Pat. No. 6,896,651; U.S. Pat. No. 6,652,449; U.S. Pat. No. 6,862,480; U.S. Pat. No. 6,712,772; and PCT Application Serial No. Unknown, filed Jun. 15, 2007, titled "Surgical Implants, Tools and Methods for Treating Pelvic Conditions" Ser. No. 12/308,436. (See International Patent Application No. PCT/US2007/014120, entitled "Surgical Implants, Tools, and Methods for Treating Pelvic Conditions, filed Jun. 15, 2007, the entirety of which is incorporated herein by reference.) PCTUS2007/004015, filed Feb. 16, 2007, titled Surgical Articles and Methods for Treating Pelvic Conditions, the entirety of which is incorporated herein by reference. WO 2007/016083, published Feb. 8, 2007, and entitled "Methods and Symptoms for Treatment of Prolapse," the entirety of which is incorporated herein by reference); including tissue at or near an ischial spine, e.g., at a region of an ischial spine.

Embodiments of exemplary implants that may be useful as discussed herein and in the incorporated references can include a tissue support portion 51 and no extension portions 58. Other embodiments can include one, two, three, or more extension portions 58 attached to a tissue support portion 51. An exemplary urethral sling can be an integral mesh strip or hammock with supportive portions consisting of or consisting essentially of a tissue support portion 51 and zero, one, or two extension portions 58.

An implant may include portions or sections that are synthetic or of biological material (e.g., porcine, cadaveric, etc.), and that may be resorbable or non-resorbable. Extension portions may be, e.g., a synthetic mesh such as a polypropylene mesh. The tissue support portion may be synthetic (e.g., a polypropylene mesh) or biologic.

The implant 44, either or both of the tissue support portion 51 or a guide extension portion 58, may comprise variable weave meshes with varying elasticities such as a mesh that is highly elastic around the anus to allow stool to pass.

Some example of commercially available materials may include MarelX™ (polypropylene) available from Bard of Covington, R.I., Prolene™ (polypropylene) and Mersilene (polyethylene terephthalate) Hernia Mesh available from Ethicon, of New Jersey, Gore-TeX™ (expanded polytetrafluoroethylene) available from W. L. Gore and associates, Phoenix, Ariz., and the polypropylene sling material available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon.

Dimensions of an implant can be as desired and useful for any particular installation procedure, treatment, patient anatomy, to support a specific tissue or type of tissue, and to extend to a desired location of internal supportive tissue or an external incision. Exemplary dimensions can be sufficient to allow the tissue support portion to contact tissue of the levator, coccygeus, rectum, external anal sphincter, etc., or any desired portion of one or more of these. Optionally, one or more guide extension portions 58 can extend from the tissue support portion 51 to a desired internal or external anatomical location to allow the guide extension portion 58 to be secured to anatomy of the pelvic region, to support the tissue support portion 51.

Dimensions of guide extension portions 58 according to the invention can allow the guide extension portion 58 to reach between a tissue support portion 51 placed to support tissue of the pelvic floor (at an end of the extension portion connected to the tissue support portion) and a location at which the distal end of the guide extension portion 58 pass through an external incision.

An implant 44 can be of a single or multiple pieces that is or are shaped overall to match a portion of the levator, e.g., that is completely or partially circular, trapezoidal (non-symmetric or symmetric), rectangular, rhomboidal, etc. The implant may be multiple pieces to fit beside or around pelvic features such as the rectum or anus. Alternately, the implant 44 may be irregular (while optionally symmetrical) to reach different areas of the levator.

To contact tissue of the pelvic floor, the implant 44 or any portion thereof can be a continuous or a non-continuous sling, and of one or multiple pieces or segments. A continuous implant may be substantially continuous between edges, to be placed over a level surface area of levator tissue. A non-continuous implant may include breaks or cuts that allow much of the implant to be placed on a level surface of levator tissue, with portions being formed to extend around tissue structure extending from or to the levator tissues, such as the anus, rectum, etc.

An embodiment of a non-continuous sling may be designed to cover or contact area of the levator, coccygeus, or both, and also reach around to contact a posterior side of the rectum or external anal sphincter. For example, a portion of an implant could attach to the lateral sides of the external anal sphincter and extend toward or in the direction of the obturator foramen, or any other suspensory structure (e.g., supportive tissue), but need not engage tissue of the obturator foramen directly. In this embodiment, the tissue support portion of the implant need not necessarily be directly under the anus to provide the corrective action for fecal incontinence. An advantage to of this approach is to allow the anus to expand unrestricted to facilitate normal rectal function and may give the levator plate (or plates) the support necessary to be leveraged.

Embodiments of implants can include a segment that is located anterior to the anus, such as in contact with levator tissue or tissue of the perineal body, anterior to the anus. Alternate implants may be designed to replace the perineal muscle or attach to the superior portion of the external sphincter. The various embodiments disclosed herein are also applicable to men and can be implanted via an incision in the perineal floor (see attached figures).

An implant, e.g., at a tissue support portion 51 can optionally include a tissue fastener such as a soft tissue anchor, a self-fixating tip, a biologic adhesive, a tissue clamp, opposing male and female connector elements that securely engage when pushed together, or any other device to secure a distal end of an extension portion to tissue of the pelvic region. Exemplary tissue fasteners are discussed, e.g., in PCT/SU2007/014120 "Surgical Implants, Tools, and Methods for Treating Pelvic Conditions, filed Jun. 15, 2007; the entirety of which is incorporated herein by reference. The implant may also have extension portions that do not include a tissue fastener at a distal end thereof, for example if the distal end is designed to be secured to tissue by other methods (e.g., suturing), or is intended to pass through a tissue path ending in an external incision. Exemplary self-fixating tips are described, for example, in PCT/US2007/004015 "Surgical Articles and Methods for Treating Pelvic Conditions," filed Feb. 16, 2007, the entirety of which is incorporated herein by reference.

A self-fixating tip 56 can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

Alternate embodiments of self-fixating tips 56 do not require and can exclude an internal channel for engaging a delivery tool 48. These alternate embodiments may be solid, with no internal channel, and may engage a delivery tool 48, if desired, by any alternate form of engagement, such as, for example, by use of a delivery tool 48 that contacts the self-fixating tip 56 at an external location such as by grasping the base (on a side or at the face of the proximal base end) or by contacting a lateral extension.

Examples of commercial implants include those sold by American Medical Systems, Inc., of Minnetonka Minn., under the trade names Apogee®, Perigee®, and Elevate™ for use in treating pelvic prolapse (including vaginal vault prolapse, cystocele, enterocele, etc.), and Sparc®, Bioarc®, Monarc®, and MiniArc™ for treating urinary incontinence. Implants useful according to the present description can include one or more features of these commercial implants.

Generally, transobturator tissue approaches are described at pending application Ser. No. 11/347,047 "Transobturator Methods for Installing Sling to Treat Incontinence, and Related Devices," filed Feb. 3, 2006, and at US publication 2005/0143618 (Ser. No. 11/064,875) filed Feb. 24, 2005, the entireties of these being incorporated herein by reference.

Also straight, helical and curved needles, as described in U.S. Publication no. 2005/0250977; 2005/0245787 and 2004/0039453, which are herein incorporated by reference in their entirety, can also be used with their associated tunneling paths and techniques.

In a related embodiment, a depth limiting feature such as a sheath design or a mechanical stop or a bend in the needle to facilitate correct depth placement. Also inside out as opposed to the outside in implantation approach is a possible variation to the described embodiments (similar to the ISCP methods and techniques).

Examples of various tissue paths, relevant anatomy, implant materials, features of implants (e.g., connectors, tensioning devices), insertion tools, are described, for example, in U.S. Publication Nos. 2002/0161382 (Ser. No. 10/106,086) filed Mar. 25, 2002; 2005/0250977 (Ser. No. 10/840,646) filed May 7, 2004; and 2005/0245787 (Ser. No. 10/834,943) filed Apr. 30, 2004; 2005/0143618 (Ser. No. 11/064,875) filed Feb. 24, 2005; and U.S. Pat. No. 6,971,986 (Ser. No. 10/280,341) filed Oct. 25, 2002; U.S. Pat. No. 6,802,807 (Ser. No. 09/917,445) filed Jul. 27, 2001; U.S. Pat. No. 6,612,977 (Ser. No. 09/917,443) filed Jul. 27, 2001; U.S. Pat. No. 6,911,003 (Ser. No. 10/377,101) filed Mar. 3, 2003; U.S. Pat. No. 7,070,556 (Ser. No. 10/306,179) filed Nov. 27, 2002, PCT/US2007/004015 "Surgical Articles and Methods for Treating Pelvic Conditions," filed Feb. 16, 2007; PCT/US2007/014120 "Surgical Implants, Tools, and Methods for Treating Pelvic Conditions, filed Jun. 15, 2007; the entireties of each of these being incorporated herein by reference.

The invention claimed is:

1. A method of supporting tissue of the pelvic floor, the method comprising
    creating an external skin incision proximate an obturator foramen that allows access to a region of tissue of the pelvic floor,
    providing a pelvic implant comprising a tissue support portion comprising a first end and a second end, a tissue fastener disposed on the first end;
    connecting the tissue fastener to a delivery tool;
    passing the implant and an end of the delivery tool through the incision,
    passing the tissue fastener and at least a portion of the tissue support portion through the obturator foramen, and
    placing the tissue support portion at the region of pelvic floor tissue;
    securing the tissue fastener to tissue of the pelvic region, and
    placing a support backer member on the second end to apply tension to the tissue support portion to support the tissue of the pelvic floor.

2. The method of claim 1 comprising placing the support portion in a portion of a muscle selected from the group comprising:
    pubococcygeus muscle;
    iliococcygeus muscle; and
    coccygeus muscle.

3. The method of claim 1 wherein the method is selected from the group comprising:
    a method of treating fecal incontinence;
    a method of supporting a perineal body,
    a method of perineal body repair;
    a method of treating levator avulsion;
    a method of treating levator ballooning;
    a method of supporting levator ani muscle;
    a method of levator ani muscle repair;
    a method of tightening or reducing the size of a levator hiatus;
    a method of treating vaginal prolapse; and
    and combinations of one or more of these.

4. A method according to claim 1 wherein the implant further comprises an extension guide portion extending from the tissue support portion, and the support backer member being guided along the extension guide portion to engage the tissue support portion.

5. A method according to claim 4 comprising a portion of the extension guide portion extending out of the incision proximate the obturator foramen and guiding the support backer member along a length of the extension guide portion and into the incision to abut a muscle of the obturator foramen.

6. The method of claim 4 wherein the tissue support portion comprises an elongate mesh, the first end comprises the mesh, the second end comprises the mesh, the tissue fastener is fixedly connected to the mesh at the first end, and the extension guide portion is fixedly connected to the mesh at the second end.

7. A method according to claim 1 comprising extending a portion of the implant through a tissue path between levator ani muscle and obturator internus muscle and abutting the support backer member against the obturator internus muscle.

* * * * *